United States Patent [19]
Marcilly et al.

[11] 3,980,727
[45] Sept. 14, 1976

[54] PROCESS FOR PRODUCING XYLENES OF HIGH PARA-XYLENE CONTENT

[75] Inventors: Christian Marcilly, Montesson; Germain Martino, Poissy; Jean-Pierre Franck, Bougival, all of France

[73] Assignee: Institut Francais du Petrole, des Carburants et Lubrifiants et Entreprise de Recherches et d'Activities Petrolieres Elf, Rueil-Malmaison, France

[22] Filed: Mar. 19, 1975

[21] Appl. No.: 559,796

[30] Foreign Application Priority Data
Mar. 20, 1974 France .............................. 74.09795

[52] U.S. Cl. ........................ 260/672 T; 260/668 A
[51] Int. Cl.² .............................................. C07C 3/62
[58] Field of Search .................... 260/672 T, 668 A

[56] References Cited
UNITED STATES PATENTS
2,966,529   12/1960   Haensel et al .................... 260/672 T
3,772,397   11/1973   Rausch ........................... 260/668 A Primary Examiner—C. Davis
Attorney, Agent, or Firm—Millen, Raptes & White

[57] ABSTRACT

Toluene and poly-methyl benzene hydrocarbons are reacted in the presence of an improved catalyst containing a group VIII noble metal. The catalyst is obtained by admixing a catalyst carrier with a Group VIII noble metal or compound thereof and with a hydrocarbyl aluminum halide. Sulfur may be present. The yield and selectivity are substantially improved as compared to conventional catalysts.

13 Claims, No Drawings

PROCESS FOR PRODUCING XYLENES OF HIGH PARA-XYLENE CONTENT

This invention concerns the use of an improved catalyst in the transalkylation of aromatic hydrocarbons, said catalyst resulting from contacting a catalyst carrier with a compound of a noble metal of group VIII of the periodic classification of elements and with a hydrocarbyl aluminum halide. Further, according to the invention, the transalkylation is preferably carried out in the presence of sulfur.

The reactions of transalkylation of aromatic hydrocarbons, which are the object of the present invention, are mainly those providing xylenes of high para-xylene content, particularly the transalkylation of toluene with poly-methyl benzenic hydrocarbons having 10 to 12 carbon atoms per molecule (particularly tetra-methyl benzenes).

By way of convention, the term "polymethylbenzenes" as used in the following description and claims will designate aromatic hydrocarbons substituted with several methyl radicals. Thus "polymethylbenzenes containing 10 to 12 carbon atoms per molecule" represents benzene molecules substituted with 4, 5 and 6 methyl radicals.

Transalkylation of toluene with a polymethyl benzene is a reaction essentially producing xylenes. When the polymethylbenzenes consist of a mixture of tri-methylbenzenes, the resulting mixture of xylenes contains mainly meta-xylene which is the isomer of lowest interest.

Conversely, when starting from a mixture of toluene and $C_{10}$–$C_{12}$ polymethylbenzenes, specially tetramethylbenzenes, it is possible to obtain a xylene mixture having a high content of para-xylene, which is the most widely used isomer for industry. This reaction may take place in liquid or gas phase and, in the latter case, it may be conducted in the presence of either inert gas or preferably hydrogen.

The catalysts in the presence of which the reaction is conducted, result in improved yield and selectivity of the transalkylation of toluene with $C_{10}^+$ poly-methyl-benzenes.

The catalysts which are used according to the process of this invention are obtained by contacting a catalyst carrier with a noble metal compound of group VIII and with a hydrocarbylaluminum halide.

The latter has preferably the general formula $AlX_yR_{(3-y)}$ where $y$ may be 1 or 2, X is halogen, preferably chlorine, and R is a monovalent hydrocarbon radical, for example straight or branched saturated alkyl which may, for example, contain 1–20 carbon atoms.

The carrier is contacted with the group VIII metal compound before, after or during the period of contact with the aluminum compound.

Examples of radicals R are methyl, ethyl, normal propyl, isopropyl normal isobutyl, isobutyl, phenyl, benzyl and cyclohexyl.

The following hydrocarbyl aluminum halides may be used: di-ethyl aluminum chloride, dodecylaluminum di-chloride, di-iso butyl aluminum chloride, di-phenyl aluminum fluoride, benzyl aluminum di-chloride, cyclohexyl aluminum dichloride and hexyl aluminum di-fluoride.

The hydrocarbyl aluminum halide may be a unique welldefined compound or a stoichiometrical or non-stoichiometrical mixture of several compounds; a sesquichloride may be used, for example ethyl aluminum sesquichloride of the analytical formula $Al_2Cl_3(C_2H_5)_3$.

It is necessary that the catalyst contain one or more metals or compounds, having hydrogenation activity, of the VIII th group of the periodic classification of elements. The preferred metal is a metal from the platinum group, for example Ru, Rh, Pd, Os, Ir and/or Pt. Its proportion may range from 0.05 to 2% by weight and preferably from 0.1 to 1 % by weight.

Particularly suitable metals of the platinum group are platinum and palladium. The catalyst may also comprise associations of catalytic metals, the additional metals being possible selected from other groups than group VIII, for example : platinum-iridium, platinum-ruthenium, platinum-tungsten, platinum-manganese, platinum-rhenium, platinum-palladium, platinum-iridium - thallium or platinum-iridium-manganese. The hydrogenating metal or metal compound may be supplied to the catalyst in any known manner.

For example, the metal of the platinum group may precipitate as a sulfide, or the carrier may be impregnated with chloroplatinic acid or an equivalent acid of another metal.

The preferred carriers consist of the oxides of metals from groups II, III and/or IV of the periodic classification of the elements, for example, magnesium, aluminum, titanium, zirconium, thorium or silicium oxides, taken separately or as mixtures or in admixture with oxides of other elements of the periodic classification, for example, boron or antimony. Coal or a molecular sieve in protonic form may also be used.

The preferred carrier consists mainly of alumina. Porous aluminae of large specific surface and containing hydrogen usually supposed to be in the form of hydroxy groups are particularly adapted to the manufacture of these catalysts. Very good results are obtained, for example, with aluminae prepared by calcining a $\beta$ - alumina tri-hydrate such as bayerite or a mixture of alumina of this type with other alumina hydrates, such as $\alpha$ -alumina trihydrates or gibbsite; $\alpha$ -alumina mono-hydrates or aluminae obtained by hydrolyzing alumina alcoholates may also be used. Such aluminae are generally characterized by a high specific surface, usually from 180 to 500 m²/g or even more. The catalysts of highest activity are usually obtained when this specific surface is higher than 200 m²/g, particularly higher than 300 m²/g.

Before introducing a hydrocarbyl aluminum halide, it may be important to subject the material to be halogenated to a treatment for removing, as much as possible, water and oxygen adsorbed on the catalyst carrier; calcination may be effected, provided it is conducted at such a temperature that the so-called constitution —OH groups are not removed during the treatment. Thus, as concerns alumina of specific higher than, or equal to 5 m²/g, calcination may be conducted at 200°–600°C and preferably 300°–500°C. In some cases, calcination may be followed with a treatment with hydrogen at 200°–600°C, preferably 300°–500°C, whose purpose is to reduce the noble metal carried on said oxide or incorporated thereto.

The hydrocarbyl aluminum halide is generally used as a solution in a straight or branched, saturated or unsaturated liquid hydrocarbon containing, for example, 5–20 carbon atoms, or in another inert solvent, specially a hydrocarbon halide. Pentanes, hexanes or heptanes may be used with advantage. This halide may be employed at a concentration ranging up to the limit solubility in the selected solvent.

It seems that, as a rule, a true reaction takes place between the halide and the carrier, for example, alumina. Since this reaction is usually quantitative, nearly all the halide contained in the solution as $Al\ X_y\ R_{(3-y)}$ will be found on the catalyst. It is thus useless to employ this agent in excess.

The proportion of fixed halogen may attain several tens % by weight with respect to the solid, so that a very large excess of hydrocarbyl aluminum halide, as compared to the noble metal content of the carrier, will be present.

The reaction between the carrier and the hydrocarbyl aluminum halide is preferably carried out in an atmosphere free of oxygen and/or oxygenated compounds; in fact, the halogenation agents such as, for example, hydrocarbyl aluminum chlorides $Al\ Cl_y\ R_{(3-y)}$ are pyrophoric; but it is worthwhile to mention that the halogenated catalysts obtained according to the process of the invention are not pyrophoric. It is possible to conduct the reaction in a rare gas, hydrogen, nitrogen or gaseous hydrocarbon environment, these compounds being taken individually or as mixtures and being made free of the above compounds.

The reaction produced by contacting the hydrocarbyl aluminum halide or a solution thereof with the material to be halogenated may be carried out under atmospheric pressure or another pressure, in an environment such as previously described, in gas phase or liquid phase, at a temperature usually ranging from 0° to 250°C, but which may attain 300°C, according to a static or dynamic technique.

It is remarkable that this halogenation technique may be employed at temperatures in excess of 180°C, for example at 180°–300°C. This shows that this technique differs from the known techniques comprising an introduction of aluminum trichloride into platinum alumina catalysts. At such high temperatures, indeed, aluminum trichloride would sublimate and not remain on the catalyst.

When static, the operation is of the carrier impregnation type, so that it may be conducted in the dry or wet manner.

In the case of a dynamic operation, the solution of the halogenating agent may be circulated on the material to be halogenated, arranged in fixed bed, at a hourly feed rate of, for example, 1–100 liters of solution per kilogram of catalyst to be halogenated.

The latter technique is usually preferred since it permits to halogenate the catalyst carrier within the reactor itself, to make use of a minimum amount of solvent, taking the solubility into account, irrespective of the proportion of halogen to be introduced into the catalyst, by continuous recycling of the solution and, finally, to use the hydrocarbon charge to be transformed by the catalyst as solvent of the halogenation agent without substantial loss of starting material.

Thus, as concerns chlorination, it is possible to introduce from 1 to 20 % by weight of chlorine into a catalyst, preferably 4–12 %, depending on the nature and surface of the carrier. When using a halide other than a chloride, the proportion of fixed halogen is of the same order of magnitude.

It is also possible to introduce a portion of the halogen according to the present method and another portion according to another known method.

A preferred catalyst may be obtained by treating alumina with an amount of hydrocarbyl aluminum chloride, calculated as chlorine, of at least 3 % by weight of the alumina, so that, for example, 3–20 % of chlorine remains on the alumina. Platinum or another noble metal is introduced in a known manner, for example, by impregnation with chloroplatinic acid, either before or after said treatment, in an amount corresponding to the introduction of 0.05– 2% by weight of platinum (weight of metal element) or other noble metal into the catalyst. This treatment is usefully followed with a heating in hydrogen atmosphere at 100–600°C, so that the platinum compound is reduced to platinum metal. A catalyst of this type may be obtained by treating a conventional platinum-on-alumina reforming catalyst according to the process of the invention.

During the transalkylation, a halogenated promoter may be introduced continuously or periodically into the feed charge, i.e. in a mixture of toluene and polymethyl benzene, said promoter being selected from the free halogens, the halohydric acids and the hydrocarbyl halides, for example, hydrochloric acid, chlorine, hydrofluoric acid or an alkyl halide, for example, ethyl chloride, iso-propyl chloride, tert-butyl chloride, chloroform, dichloromethane, methyl chloride, trichloroethylene or tert-butyl bromide in an amount of, for example, 10 to 10,000 ppm by weight of the hydrocarbon charge. Higher proportons may be used but do not usually result in a significant advantage.

The alkyl halides contain, for example, 1–6 carbon atoms per molecule.

It has been observed that halogen, when introduced as a halide promoter, can be found in totality or at least in a large proportion in the reactor outflow, either as such or in the form of halohydric acid. This promoter or the transformation products thereof may thus be recovered at the outlet of the reaction zone and recycled to the inlet of the same zone; it suffices to add fresh promoter, either periodically or continuously, in low proportion, for example 10 to 100 ppm by weight of the hydrocarbon charge, to compensate for the losses.

According to the invention, it has also been observed that the reaction of para-xylene production is considerably improved when operating in the presence of selected amounts of sulfur. Sulfur may be supplied either to the catalyst or to the charge, for example by continuous injection of a sulfur compound.

The continuous or discontinuous sulfuration of the feed charge may be carried out by means of sulfur-containing molecules present in the charge such as, for example, mercaptans, dialkylsulfides, thiophane or dibenzothiophane. Sulfuration of the catalyst prior to its use in the conversion of aromatics may be carried out with hydrogen sulfide and/or one or more of the above-mentioned sulfur compounds; this previous sulfuration of the catalyst is preferably continued in the course of the reaction by means of one or more of the above-mentioned sulfur compounds.

When using a sulfurized catalyst, the latter preferably contains 0.002 to 2 % and particularly, 0.01 to 1 %, of sulfur by weight of the catalyst.

When sulfur is directly introduced into the feed charge, the latter preferably contains 0.005 to 2 % and particularly, 0.01 to 0.5 % of sulfur by weight of the feed charge.

Operating in the presence of sulfur is particularly suitable for the reactions of transalkylation of aromatics at low temperature and results specially in overall selectivities to para-xylenes higher than those obtained either with similar catalysts free of noble metals or with sulfurfree catalysts containing noble metals.

Catalysts such as hereinbefore described may be used for transalkylating toluene with $C_{10}$–$C_{12}$ polymethylbenzenes in the liquid or gas phase at a temperature usually in the range of from 50° to 350°C and preferably in the range of from 100° to 250°C. Preferred conditions include a pressure from 1 to 100 kg/cm$^2$ and a space velocity of 0.2 to 10 liters of charge per liter of catalyst and per hour.

At reaction temperatures of from 50° to 200°C, the operation may be conducted at will either in liquid or gas phase; when working in gas phase, it is preferred to operate in the presence of hydrogen, rather than inert gas, with a catalyst which is continuously sulfurated and at a molar ratio or $H_2$ to the feed charge of 2 to 10. When working at temperatures below 200°C, the operation is preferably conducted only in the liquid phase.

The following examples illustrate the invention but do not limit the scope thereof.

EXAMPLE 1

Manufacture of catalyst A 100 g of reforming catalyst containing 0.35 % by weight of platinum on an alumina carrier having a specific surface of 416 m$^2$/g and a pore volume of 0.6 cc/g, previously calcined for one hour in air at 400°C, is charged into a stainless steel reactor of the Grignard type, equipped with a device for injection of a liquid compound under pressure and controlled atmosphere. After rapid closure of the reactor, vacuum is made for one hour in the reactor by means of a pump. The reactor is then pressurized with argon.

While the temperature is maintained at 50°C and the pressure at 2 bars abs., 200 cc of a solution containing one mole of dichloro ethyl aluminum per liter of normal hexane is supplied to the reactor.

After stirring for half and hour at 50°C under argon atmosphere, the solvent is discharged and the solid is dried. The resulting product contains about 0.3 % by weight of platinum and 11.9 % by weight of chlorine and constitutes catalyst A.

EXAMPLE 2

Manufacture of catalyst B

While using the same alumina as before, but free of noble metal, we proceed in the same manner as for producing catalyst A.

The resulting product (catalyst B) contained about 11.9% by weight of chlorine.

EXAMPLE 3

Transalkylation of toluene in the gas phase by means of tetramethylbenzenes ($T_4MB$)

Catalyst A, prepared in the manner described in example 1, is used for transalkylating toluene by means of 1,2,4,5-tetramethylbenzene (1,2,4,5 $T_4MB$) in the vapor phase, in the presence of nitrogen. The charge consists of a mixture of toluene and 1,2,4,5-tetramethylbenzene in the molar proportion of 85/15 (i.e. 79.5/20.5 by weight), said mixture also containing 500 ppm of carbon tetrachloride.

The operating conditions are the following :
Temperature : 150°C, VVH : 1, pressure : 5 bars, nitrogen in a molar ratio of $N_2$ to the feed charge of 5.
The results are reported in Table I.

TABLE I

| T°C | Time (hour) | % aromatics in the effluent | % conversion of $T_4MB$ | % xylenes | % TMB | % para-xylene in the xylenes |
|---|---|---|---|---|---|---|
| 150 | 4 | 98.6 | 35 | 9.5 | 7.4 | 40.7 |
| 150 | 8 | 100 | 0 | — | — | — |

EXAMPLE 4

Transalkylation of toluene by means of tetramethylbenzenes ($T_4MB$) in the gas phase Catalyst A, prepared according to example 1, is used for transalkylation of toluene with 1,2,4,5-tetramethylbenzene (1,2,4,5 $T_4MB$) in the vapor phase but in the presence of hydrogen and not nitrogen as in example 3. The feed charge is identical to that of example 3. The operating conditions are the following :
Temperature : 150°C, VVH of from 1 to 3, pressure :5 bars (hydrogen pressure), the molar ratio $H_2$/HC being 5.

The results are given in Table II

TABLE II

| T°C | Time (hour) | VVH | % aromatics in the effluent | % conversion of $T_4MB$ | % xylenes | % TMB | % paraxylene in the xylenes |
|---|---|---|---|---|---|---|---|
| 150 | 4 | 1 | 24.3 | 51.0 | 2.2 | 2.8 | 47.0 |
| 150 | 8 | 3 | 41.8 | 20.1 | 0.9 | 1.1 | 58.1 |

It appears that, when operating in the presence of hydrogen (example 4), better results are obtained than when operating in the presence of an inert gas (example 3): in the presence of an inert gas, the activity decreases very quickly.

EXAMPLE 5

Transalkylation of toluene by means of tetramethylbenzenes ($T_4MB$) in the vapor phase Catalyst A of example 1 is used for the transalkylation of toluene with 1,2,4,5-tetramethylbenzene in the vapor phase in the presence of hydrogen, as in example 4. The feed charge is the same as in example 3 and 200 ppm of thiophene are added thereto. The operating conditions are following:

Temperatures of from 150° to 170°C, VVH of from 1 to 5, pressure: 5 bars, molar ratio of $H_2$ to the feed charge from 2.5 to 5.

The results are given in Table III.

TABLE III

| T°C | VVH | $H_2$/feed charge | Time (hour) | % aromatics in the effluent | % conversion of $T_4MB$ | % xylenes | % TMB | % para-xylenes in the xylenes |
|-----|-----|-------------------|-------------|-----------------------------|--------------------------|-----------|-------|-------------------------------|
| 150 | 1   | 5                 | 4           | 90.7                        | 75.2                     | 12.6      | 10.3  | 45.3                          |
| 150 | 1   | 5                 | 8           | 96.8                        | 76.2                     | 12.9      | 12.0  | 47.1                          |
| 170 | 3   | 5                 | 12          | 99.7                        | 74.8                     | 12.3      | 10.3  | 47.2                          |
| 170 | 3   | 5                 | 16          | 99.7                        | 40                       | 6.6       | 7.5   | 52.0                          |
| 170 | 5   | 5                 | 20          | 99.9                        | 15                       | 1.9       | 2.1   | 67.6                          |

In the first hours of run, the inhibition of the hydrogenating activity of platinum by sulfur is insufficient, which results in substantial hydrogenation of aromatics; thereafter the performances with respect to activity and mainly stability, of the sulfurated catalyst A working in the presence of hydrogen become higher than those obtained with the corresponding sulfur-free catalyst working in the absence (example 3) or in the presence (example 4) of hydrogen.

1,2,4,5-tetramethylbenzene in the vapor phase under conditions identical to those of example 5.

The rsults are reported in Table IV.

TABLE IV

| T°C | VVH | $H_2$/feed charge | Time (hour) | % aromatics in the effluent | % conversion of $T_4MB$ | % xylenes | % TMB | % para-xylene in the effluent |
|-----|-----|-------------------|-------------|-----------------------------|--------------------------|-----------|-------|-------------------------------|
| 150 | 1   | 5                 | 4           | 99.6                        | 78.4                     | 12.9      | 11.5  | 44.1                          |
| 170 | 1   | 5                 | 8           | 99.8                        | 73.2                     | 12.5      | 11.7  | 46.9                          |
| 170 | 3   | 5                 | 12          | 99.9                        | 43.1                     | 8.0       | 7.9   | 50.6                          |

This example shows that a previous sulfuration of the catalyst prevents hydrogenation of aromatics in the first hours of the experiment.

EXAMPLE 7

Transalkylation of toluene with tetramethylbenzene in the liquid phase

Catalyst A is used for transalkylation of toluene with 1,2,4,5-tetramethylbenzene in the liquid phase. The feed charge is the same as in example 5. The operating conditions are the following:

Temperatures of 150°–170°C, VVH of 1–5, hydrogen pressure: 40 bars, hydrogen feed rate: 0.

The results are reported in table V.

TABLE V

| T°C | VVH | Time (hour) | % aromatics in the effluent | % conversion of $T_4MB$ | % xylenes | % TMB | % para-xylene in the effluents |
|-----|-----|-------------|-----------------------------|--------------------------|-----------|-------|--------------------------------|
| 150 | 1   | 4           | 86.5                        | 82.0                     | 13.5      | 12.6  | 49.7                           |
| 170 | 3   | 8           | 97.8                        | 71.7                     | 11.9      | 10.4  | 51.1                           |
| 170 | 3   | 12          | 99.9                        | 69.9                     | 11.4      | 10.5  | 51.9                           |

EXAMPLE 6

Transalkylation of toluene with tetramethylbenzen ($T_4MB$) in the vapor phase

The catalyst A of example 1 is subjected for 15 minutes to a treatment at 150°C with a mixture of hydrogen and hydrogen sulfide (molar ratio of $H_2$ to $H_2S$ : 10) passing over the catalyst at a rate of 100 liters per hour. The resulting catalyst contains 0.085 % by weight of sulfur. It is then used for transalkylation of toluene with

EXAMPLE 4 A

Transalkylation of toluene with tetramethylbenzenes in the gas phase on catalyst free of noble metal Catalyst B is used for transalkylation of toluene with 1,2,4,5-tetramethyl benzene in the gas phase. The charge is the same as in example 3. The operating conditions are those of example 4. The results are reported in table VI.

TABLE VI

| T°C | VVH | $H_2$/Hc | Time (hour) | % aromatics in the effluents | % Conversion of $T_4MB$ | % xylenes | % TMB | % para-xylene in the efflu. |
|-----|-----|----------|-------------|------------------------------|--------------------------|-----------|-------|-----------------------------|
| 150 | 1   | 5        | 4           | 99.5                         | 30.6                     | 5.7       | 4.9   | 33.4                        |
| 170 | 1   | 5        | 8           | 99.9                         | 65.2                     | 10.4      | 9.0   | 30.4                        |
| 170 | 3   | 5        | 12          | 99.9                         | 33.5                     | 6.1       | 5.2   | 32.6                        |
| 170 | 5   | 5        | 16          | 99.9                         | 14.1                     | 3.2       | 2.0   | 37.9                        |

This example shows that the noble metal containing catalyst A gives better results than catalyst B, with respect to both activity and selectivity.

What we claim is:

1. Process for transalkylating toluene with a polymethyl benzene hydrocarbon containing from 10 to 12 carbon atoms in the presence of a catalyst obtained by contacting a catalyst carrier with at least one group VIII noble metal or compound thereof and with a hydrocarbyl aluminum halide of the formula $AlX_yR_{(3-y)}$ in which $y$ is 1 or 2, X is halogen and R is a monovalent hydrocarbon radical.

2. A process according to claim 1, wherein the noble metal is present in an amount of 0.05 to 2 % by weight, as the metal element, with respect to the catalyst, the catalyst carrier being alumina.

3. A process acording to claim 2 comprising contacting the carrier with the hydrocarbyl aluminum halide at a temperature from 0° to 250°C.

4. A process according to claim 1, comprising a first step of contacting the carrier with the noble metal or compound thereof, a second step consisting of a treatment with hydrogen at 100°–600°C and a third and final step of contact with the hydrocarbyl aluminum halide.

5. A process according to claim 1, wherein the transalkylation is carried out in gas or liquid phase at a temperature of from 50° to 350°C.

6. A process according to claim 5, conducted at a temperature from 100° to 250°C.

7. A process according to claim 5, conducted in the presence of hydrogen.

8. A process according to claim 1, wherein the transalkylation is carried out in gas phase, in the presence of hydrogen, at a temperature from 50° to 200°C.

9. A process according to claim 1, wherein the feed charge consisting of a mixture of toluene and polymethyl benzene hydrocarbon contains 0.005–2 % of sulfur by weight.

10. A process according to claim 9, wherein the feed charge contains 0.01–0.5 % of sulfur by weight.

11. A process according to claim 1, wherein the catalyst contains 0.002–2 % of sulfur by weight.

12. A process according to claim 11, wherein the catalyst contains 0.01–1 % of sulfur by weight.

13. A process according to claim 1, wherein the transalkylation is performed, in the presence of a halide promoter selected from the free halogens, the halohydric acids and the hydrocarbyl halides, usd in an amount of 10–10,000 parts by weight of the hydrocarbon charge.

* * * * *

UNITED STATES PATENT AND TRADEMARK OFFICE
CERTIFICATE OF CORRECTION

PATENT NO. : 3,980,727
DATED : September 14, 1976
INVENTOR(S) : Christian Marcilly et al.

It is certified that error appears in the above-identified patent and that said Letters Patent are hereby corrected as shown below:

[73] Assignee: show read --INSTITUT FRANCAIS DU PETROLE--.

Signed and Sealed this

First Day of February 1977

[SEAL]

Attest:

RUTH C. MASON
*Attesting Officer*

C. MARSHALL DANN
*Commissioner of Patents and Trademarks*